United States Patent
Gregg, Jr.

(10) Patent No.: US 6,541,044 B1
(45) Date of Patent: Apr. 1, 2003

(54) KAVA-KAVA ROOT COMPOSITION AND ASSOCIATED METHODS

(75) Inventor: Fred B. Gregg, Jr., Leesburg, FL (US)

(73) Assignee: U.S. Nutraceuticals, Leesburg, FL (US)

( * ) Notice: Subject to any disclaimer, the term of this patent is extended or adjusted under 35 U.S.C. 154(b) by 0 days.

(21) Appl. No.: 09/715,833

(22) Filed: Nov. 17, 2000

Related U.S. Application Data

(60) Provisional application No. 60/166,584, filed on Nov. 19, 1999.

(51) Int. Cl.[7] ............................................. A61K 35/78
(52) U.S. Cl. ....................... 424/734; 424/773; 210/634
(58) Field of Search ................................ 424/734, 773; 210/634

(56) References Cited

U.S. PATENT DOCUMENTS

| | | |
|---|---|---|
| 5,932,101 A | 8/1999 | Kanel et al. |
| 6,106,720 A | 8/2000 | Kanel et al. |

OTHER PUBLICATIONS

Ashraf–Khorassani et al. Chromatographia (Sep. 1999), vol. 50, No. 5/6, pp. 287–292.*

Lopez–Avila et al. J. High Resol. Chromatogr. (1997), vol. 20, No. 10, pp. 555–559.*

* cited by examiner

*Primary Examiner*—Leon B. Lankford, Jr.
*Assistant Examiner*—Susan D. Coe
(74) *Attorney, Agent, or Firm*—Allen, Dyer, Doppelt, Milbrath & Gilchrist, P.A.

(57) ABSTRACT

A method of making an extract from kava-kava root includes drying the kava-kava root, and grinding the dried root to a powder. Compounds are extracted by contacting the ground root with $CO_2$ at an extraction pressure of at least about 500 bar, and at a temperature of less than about 65° C. The dissolved kava-kava compounds are separated from the $CO_2$ into at least a first fraction by collecting the carbon dioxide after extracting and decreasing the pressure to a predetermined first separation pressure lower than the extraction pressure, at a temperature sufficient to prevent the carbon dioxide from solidifying. A composition including a kava-kava extract comprises greater than about 70% kavalactone, greater than about 0.3% flavokawin, and preferably comprises about 30% flavokawin. The composition comprises substantially no solvent residue and includes a pharmaceutically acceptable carrier. The composition is taken orally for nutritinal supplementation in a substantially soft gel capsule.

12 Claims, 1 Drawing Sheet

KAVA-KAVA ROOT COMPOSITION AND ASSOCIATED METHODS

RELATED APPLICATION

This application claims priority from co-pending provisional application Serial No. 60/166584, which was filed on Nov. 19, 1999.

FIELD OF THE INVENTION

The present invention relates to the field of nutritional supplements and, more particularly, to a composition comprising an extract of kava-kava root and a method for the extraction of kava-kava root compounds.

BACKGROUND OF THE INVENTION

Supercritical $CO_2$ has been used for about 20 years to extract non-polar compounds such as lipids, including fatty acids and sterols from solid plant material. Typical products of supercritical fluid extraction (SFE) include decaffeinated coffee and tea, essential oils from hops used in brewing, and extraction of aromas and flavors from spices and herbs.

The technology of supercritical $CO_2$ extraction advantageously employs the increased dissolving power of $CO_2$ increases at high pressures. At pressures less than the critical pressure of $CO_2$, solubilities are essentially nil, but as the pressure is increased to several thousand pounds per square inch, the $CO_2$ has the dissolving power of a liquid, but the flow characteristics of a gas. Thus, $CO_2$ can easily flow through a pressurized extraction vessel containing powdered kava-kava root and quickly dissolve the non-polar oily constituents. The product-laden $CO_2$ then flows to a separation vessel where pressure is lowered and the $CO_2$ passes off as a gas, leaving the extract behind as recovered product. The $CO_2$ is recycled, compressed, and the process repeated.

Herbal products such as kava-kava root extract have long been used as home remedies and dietary supplements in many parts of the world. Kava-kava root has previously been extracted through a standard method using ethanol as the solvent. This prior art process results in an extract providing an insufficient yield of kavalactones, which comprise the desired components of kava-kava root. In addition, ethanol extracts of the root have the further undesirable property of including a certain amount of the solvent in the final product. The typical extraction process of the kava-kava root for kavalactones produces a yield of about 40–50% kavalactones, and a yield of at most 0.3% of flavokawain. The average industry percentage of kavalactone of a kava-kava extract is less than 70% and contains harmful solvent residue.

The present invention relates to herbal extracts and processes for herbal extracts. More specifically, it relates to herbal extracts of whole kava-kava root to obtain a liquid, semi-solid extracts, and/or paste extracts whereby these extracts are obtained through a supercritical carbon dioxide fluid extraction process.

SUMMARY OF THE INVENTION

With the foregoing in mind, the present invention advantageously provides a method for extracting kava-kava root, a composition comprising the extract, and a method of nutritional supplementation employing the extract.

Supercritical fluid extraction of kava-kava (*Piper methysticum*) at a preferred pressure and temperature yields a paste extract having a much higher percentage of kavalactone and flavokawain than is obtainable with previous processes. When the extraction process is conducted according to the present invention, at a pressure above 500 bar and a temperature range of 450° C. to 65° C., the extract is separated from the $CO_2$ in the form of a paste having a kavalactone percent by weight of greater than 70% and a flavokawain of approximately 30% by weight. The kava-kava extract contains kavalactones at percentages surprisingly higher than industry standard.

Other than the present invention, kava extraction is generally conducted by producing a dry extract using conventional liquid solvents in the extraction process, and particularly ethanol. Supercritical CO2 has been previously employed for extracting kava-kava root, but at the pressures employed, substantially lower than 500 bar, recovery of kavalactones is not significantly higher than with ethanol extraction. The present invention employs supercritical fluid extraction at higher pressures to achieve its unexpectedly higher kavalactone concentrations. The kavalactone percentage by weight in the kava extract obtained in this inventive process is greater than 70% with no harmful solvent residue.

In the present invention, whole, dried kava root is ground to a fineness of from about minus 40 to about plus 60 mesh. The supercritical carbon dioxide extraction process is conducted at pressures of at least 500 bar, and at temperatures from 45° C. to 65° C. The high pressure and relatively low temperature conditions increase yields of the desired kava compounds while preserving favorable qualities of the extract produced, for example, resulting in an extract having a relatively low oxidation state.

BRIEF DESCRIPTION OF THE DRAWINGS

Some of the features, advantages, and benefits of the present invention having been stated, others will become apparent as the description proceeds when taken in conjunction with the accompanying drawings in which.

DETAILED DESCRIPTION OF THE PREFERRED EMBODIMENT

Figure 1:
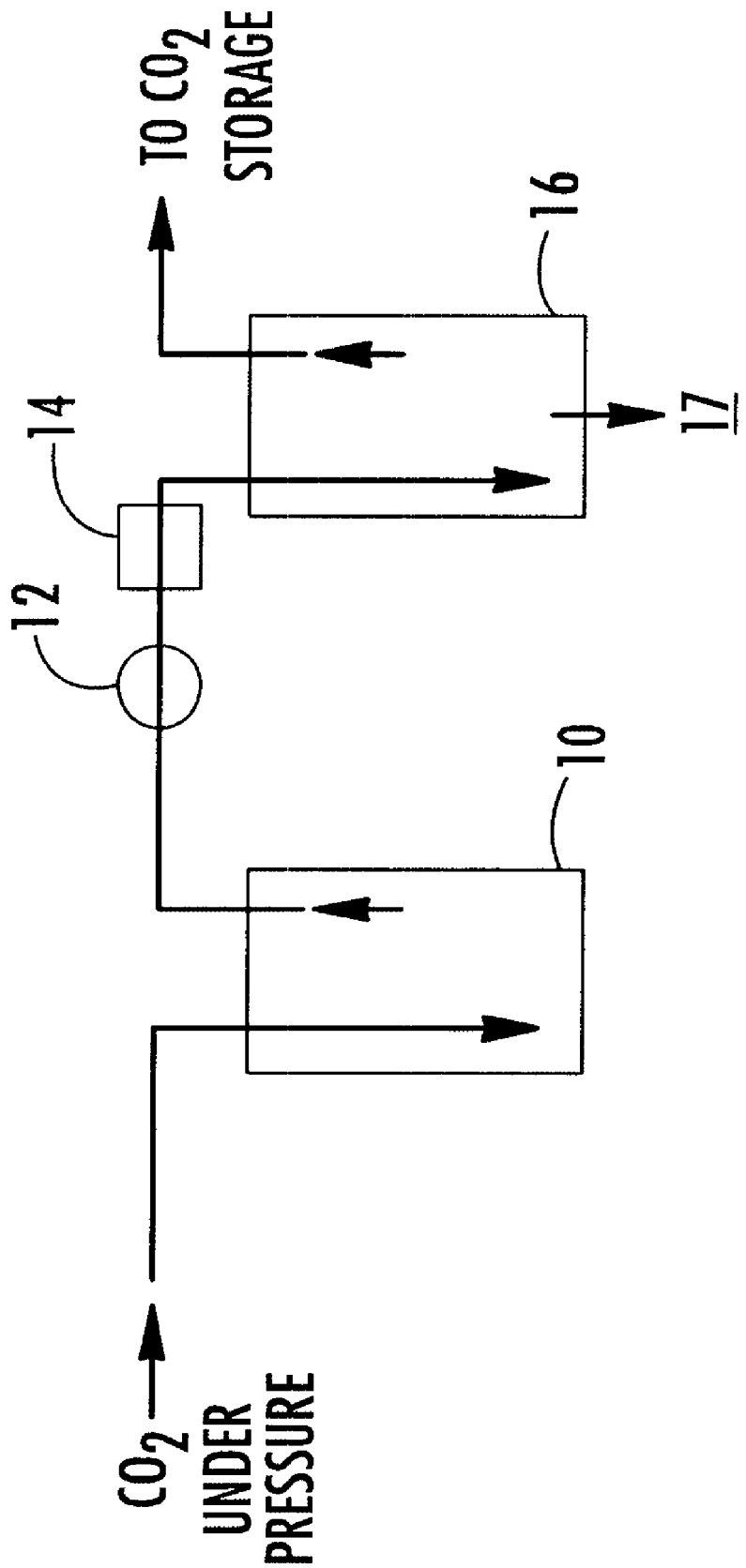
FIG. 1 is a schematic diagram of the kava-kava root extraction process according to an embodiment of the present invention.

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art.

The present invention includes a method of making an extract from kava-kava root. The method comprises drying the kava-kava root, and grinding the dried root. The ground root is then extracted by contacting the ground root with carbon dioxide at an extraction pressure of at least 500 bar, and at a temperature of less than about 65° C. The extraction dissolves kava-kava compounds into the carbon dioxide. Extracting the ground kava-kava root is effected by contacting the ground material with $CO_2$ under pressure and substantially as a continuous flow of carbon dioxide, preferably at a temperature of from about 45° C. to about 65° C.

FIG. 1 schematically illustrates the extraction method of the invention. $CO_2$ flows into the extraction vessel 10 from a source of high pressure $CO_2$. The extraction vessel 10 is loaded with ground kava-kava root, and the $CO_2$ is delivered into the vessel so that it must flow through the loaded product before being discharged from the vessel. As the high pressure $CO_2$ flows through the product, it behaves as a solvent and extracts kava-kava compounds which are soluble in the fluid.

After extracting, the method continues by separating the dissolved kava-kava compounds from the $CO_2$ into at least a first fraction by collecting the carbon dioxide after extracting. As shown in FIG. 1, from extraction vessel 10, $CO_2$ flows through a pressure reducer 12, the temperature of the $CO_2$ being regulated by a temperature regulator 14. The $CO_2$ is then conducted into a separation vessel 16 from which a fraction 17 is collected. Separation is accomplished by decreasing the pressure of the $CO_2$ to a predetermined first separation pressure lower than the extraction pressure, at a temperature sufficient to prevent the carbon dioxide from solidifying. Upon decreasing the pressure, dissolved compounds will come out of solution and they may be collected from the separation vessel 16, as fraction 17. Following the separation, the $CO_2$ is returned to storage for further use.

In the extraction method, grinding preferably comprises grinding the dried kava-kava root substantially to a fineness of about from −40 to about +60 mesh. Most preferably, grinding comprises grinding the dried kava-kava root substantially into a powder. Extraction is conducted at a pressure of at least 500 bar, and above. Separation is conducted at pressures lower than the extraction pressure, and may be predetermined for collecting desired fractions of kava-kava root compounds.

As shown in Table 1, the extraction method of the present invention results in an extract having a

TABLE 1

SUPERCRITICAL FLUID EXTRACTION (SFE) OF KAVA KAVA ROOT

|  | RAW MATERIAL | ETH-ANOL | SUPERCRITICAL | | |
| --- | --- | --- | --- | --- | --- |
| EXTRACTION PRESSURE |  |  | 300 Bar | 500 Bar | 620 Bar |
| EXTRACTION TEMPERATURE |  | 20° C. | 50° C. | 50° C. | 50° C. |
| TOTAL YIELD |  | 7.50% | 5.50% | 6.50% | 7.10% |
| COMPOSITION (in %) |  |  |  |  |  |
| desmethoxy-yangonin | 0.54 | 3.26 | 2.60 | 5.56 | 6.80 |
| dihydrokawain | 1.78 | 10.86 | 13.40 | 15.90 | 21.70 |
| ihydromethysticin | 0.95 | 11.84 | 7.19 | 12.82 | 11.00 |
| kawain | 1.75 | 13.51 | 10.40 | 21.10 | 21.80 |
| methysticin | 0.78 | 3.00 | 4.19 | 8.33 | 9.10 |
| Yangonin | 0.95 | 7.36 | 3.46 | 11.80 | 9.80 |
| TOTAL KAVALACTONES | 6.75 | 49.83 | 41.24 | 75.51 | 80.20 |
| LACTONE YIELDS | 6.75 | 3.74 | 2.27 | 4.91 | 5.69 |
| RECOVERY |  | 55.37 | 33.60 | 72.71 | 84.36 |
| Over Ethanol |  |  | 0.60 | 131.33 | 152.36 |
| Over 300 Bar SFE |  |  |  | 216.39 | 251.04 |
| Over 500 Bar SFE |  |  |  |  | 116.02 |
| COLOR |  | Brown | Yellow | Yellow | Yellow |

Composition by High Performance Liquid Chromatography against Standards.

surprisingly high yield of kavalactones. For example, an extraction at 500 bar produces an extract having about a 75% yield of total kavalactones. In contrast, the standard extraction method using ethanol produces an extract containing only about a 50% yield of kavalactones, similarly for supercritical fluid extraction at 300 bar, as shown in Table 1. Additionally, the present method produces an extract containing above a 30% yield of flavokawains (dihydrokawain and kawain, as shown in Table 1). Previous extraction methodologies result in flavokawain yields below 30%. A further benefit of the method of extraction disclosed in the present invention includes a kava-kava root extract product having generally an attractive, bright yellow color indicative of a low oxidation state. As a kava-kava extract becomes oxidized, the bright yellow color changes to a brownish color which is decidedly less appealing to the consumer. The previously available ethanol extracts of kava-kava root display this unattractive brownish color. Accordingly, the extract produced by the present invention is much more attractive in color to the consumer, thereby creating a marketing advantage.

The present invention also includes a composition including a kava-kava extract comprising greater than about 70% kavalactone, as shown in Table 1. The composition of the invention preferably comprises greater than about 30% flavokawain. Because extraction is accomplished by supercritical fluid extraction with $CO_2$, the kava-kava extract comprises substantially no solvent residue. The composition of the invention additionally may comprise a pharmaceutically acceptable carrier, and may be delivered for oral ingestion in a substantially soft gel capsule. An additional method of the invention includes a method of providing nutritional supplementation by ingestion of the kava-kava composition described herein.

In the drawing and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A method of making an extract from kava-kava root, comprising:

drying the kava-kava root;

grinding the dried root;

extracting compounds without the use of ethanol by contacting the ground root with carbon dioxide at an extraction pressure of at least about 500 bar, and at a temperature of less than about 65° C. to thereby dissolve kava-kava compounds in the carbon dioxide; and separating the dissolved kava-kava compounds from the carbon dioxide into at least a first fraction by collecting the carbon dioxide after the extraction and decreasing the pressure to a predetermined first separation pressure lower than the extraction pressure, at a temperature sufficient to prevent the carbon dioxide from solidifying.

2. The method of claim 1, wherein grinding comprises grinding the dried kava-kava root to a fineness of about from −40 to about +60 mesh.

3. The method of claim 1, wherein grinding comprises grinding the dried kava-kava root into a powder.

4. The method of claim 1, wherein the extraction pressure is at least about 550 bar.

5. The method of claim 1, wherein contacting is conducted at a temperature of from about 45° C. to about 65° C.

6. The method of claim 1, wherein extracting comprises a continuous flow of carbon dioxide.

7. The method of claim 1, wherein separating comprises a continuous flow of carbon dioxide.

8. A method of making an extract from kava-kava root, comprising:

extracting compounds without using ethanol by contacting dried, ground kava-kava root with a continuous flow of carbon dioxide at an extraction pressure of at least about 500 bar, and at a temperature of less than about 65° C. to thereby dissolve kava-kava compounds in the carbon dioxide; and separating the dissolved kava-kava compounds from the carbon dioxide by decreasing the pressure of the continuous flow of carbon dioxide after extracting to a separation pressure lower than the extraction pressure, at a temperature sufficient to prevent the carbon dioxide from solidifying.

9. The method of claim 8, wherein dried, ground kava-kava root comprises a fineness of from about −40 to about +60 mesh.

10. The method of claim 8, wherein dried, ground kava-kava root comprises a powder.

11. The method of claim 8, wherein the extraction pressure is at least about 550 bar.

12. The method of claim 8, wherein contacting is conducted at a temperature of from about 45° C. to about 65° C.

* * * * *